US010150726B2

(12) United States Patent
Nemoto et al.

(10) Patent No.: US 10,150,726 B2
(45) Date of Patent: Dec. 11, 2018

(54) METHOD FOR PRODUCING LEVULINIC ACID ESTER

(71) Applicants: UBE INDUSTRIES, LTD., Ube-shi, Yamaguchi (JP); NATIONAL INSTITUTE OF ADVANCED INDUSTRIAL SCIENCE AND TECHNOLOGY, Tsukuba-shi, Ibaraki (JP)

(72) Inventors: Koji Nemoto, Tsukuba (JP); Kenichi Tominaga, Tsukuba (JP); Kazuhiko Sato, Tsukuba (JP); Atsushi Yamada, Ube (JP); Yasushi Yamamoto, Ube (JP)

(73) Assignees: UBE INDUSTRIES, LTD., Yamaguchi (JP); NATIONAL INSTITUTE OF ADVANCED INDUSTRIAL SCIENCE AND TECHNOLOGY, Ibaraki (JP)

( * ) Notice: Subject to any disclaimer, the term of this patent is extended or adjusted under 35 U.S.C. 154(b) by 0 days.

(21) Appl. No.: 15/525,108

(22) PCT Filed: Feb. 1, 2016

(86) PCT No.: PCT/JP2016/052893
§ 371 (c)(1),
(2) Date: May 8, 2017

(87) PCT Pub. No.: WO2016/129434
PCT Pub. Date: Aug. 18, 2016

(65) Prior Publication Data
US 2017/0327453 A1    Nov. 16, 2017

(30) Foreign Application Priority Data

Feb. 13, 2015  (JP) .................................. 2015-026055
Jan. 9, 2016   (JP) .................................. 2016-003101

(51) Int. Cl.
C07C 67/08     (2006.01)
C07C 69/716    (2006.01)
C07B 61/00     (2006.01)

(52) U.S. Cl.
CPC ............ *C07C 67/08* (2013.01); *C07C 69/716* (2013.01); *C07B 61/00* (2013.01)

(58) Field of Classification Search
CPC ........ C07C 67/08; C07C 69/716; C07B 61/00
See application file for complete search history.

(56) References Cited

U.S. PATENT DOCUMENTS 5,608,105 A    3/1997   Fitzpatrick

FOREIGN PATENT DOCUMENTS

| CN | 103408422 A | 11/2013 |
|---|---|---|
| JP | 55-087741 A | 7/1980 |
| JP | 2004-359660 A | 12/2004 |
| JP | 2010-143861 A | 7/2010 |
| JP | 2010143861 * | 7/2010 |
| WO | 2009/156842 A1 | 12/2009 |
| WO | 2014/033734 A2 | 3/2014 |

OTHER PUBLICATIONS

English translation of JP2010-143861, pp. 1-11, 2010 (Year: 2010).*
Official Communication issued in International Patent Application No. PCT/JP2016/052893, dated Apr. 26, 2016.
Mckenzie, "Levulinic Acid", Organic Syntheses, A Publication of Reliable Methods for the Preparation of Organic Compounds, vol. 9, 1929, 3 pages.
Dahlmann, "Notiz über die Darstellung von Lävulinsäure", Chem. Ber. 1968, pp. 4251-4253.
Zhou et al., "Conversion of carbohydrate biomass to methyl levulinate with Al2(SO4)3 as a simple, cheap and efficient catalyst", Catalysis Communications, vol. 50, May 5, 2014, pp. 13-16.
Tominaga et al., "Mixed-acid systems for the catalytic synthesis of methyl levulinate from cellulose", Green Chemistry, vol. 13, Feb. 14, 2011, pp. 810-812.

* cited by examiner

*Primary Examiner* — Pancham Bakshi
*Assistant Examiner* — Mark R Luderer
(74) *Attorney, Agent, or Firm* — Keating & Bennett, LLP

(57) ABSTRACT

Provided is a method for efficiently producing a levulinic acid ester from a cellulose-containing raw material or a carbohydrate-containing raw material in an alcohol solvent using an inexpensive, easily available catalytic system. In a method for producing a levulinic acid ester by reacting at least one of a cellulose-containing raw material and a carbohydrate-containing raw material in the presence of an alcohol and a catalyst, use is made of, as a catalyst, a combination of: at least one metal compound (exclusive of gallium acetylacetonate and indium acetylacetonate) selected from the group consisting of hydroxide salts, sulfates, nitrates, carboxylates, alkoxides, acetylacetonates, and oxides of at least one metal selected from the group consisting of metals belonging to Group XIII and Group XIV of the Periodic Table; and an organic sulfonic acid.

9 Claims, No Drawings

METHOD FOR PRODUCING LEVULINIC ACID ESTER

TECHNICAL FIELD

This invention relates to a levulinic acid ester production technique for producing a levulinic acid ester by using carbohydrate, such as cellulose, or a carbohydrate-containing material, such as a biomass-derived material, as a raw material and reacting the carbohydrate in the presence of an alcohol and a catalyst.

BACKGROUND ART

Recently, attention has been increasingly drawn to a biomass refinery technique for systematically producing various chemicals using biomass as a raw material in place of fossil sources, such as petroleum. Particularly, levulinic acid and its esters, as chemicals producible from cellulose which is an inedible biomass source present in the greatest amount on the earth, are raw materials for basic chemicals including butene, for general-purpose resin sources including adipic acid, and for functional chemicals including agrochemicals, and their high potential as essential materials are attracting attention.

As methods for producing levulinic acid there are known methods for producing it by using sugar, such as glucose, or carbohydrate, such as starch or cellulose, as a raw material and heating the raw material in water into which hydrochloric acid, hydrobromic acid or sulfuric acid is added (see Non-Patent Literatures 1 and 2 and Patent Literatures 1 and 2). In either case, acid is required in a few or more equivalents per mole of sugar in the raw material and the product is also an organic acid, by reason of which how to prevent corrosion of the apparatus has become a major issue.

For example, Patent Literature 2 describes a method for continuously producing levulinic acid using cellulose as a raw material and sulfuric acid, in which case in order to produce levulinic acid at a yield of 70% or more, three or more equivalents of sulfuric acid is required per mole of glucose constituting cellulose. In the case of an industrial production process, how to prevent corrosion of the apparatus and the disposal of post-reaction acid become issues.

There is known as a solution to the above issues a method in which an alcohol is used as a reaction solvent to reduce the amount of acid used and synthesize a levulinic acid ester in a single stage from sugar, such as glucose, or carbohydrate, such as starch or cellulose. In this case, because the amount of acid used is required less than before and the product is an ester compound, the problems of corrosion of the apparatus and disposal of post-reaction acid are significantly reduced.

For example, according to a method in Patent Literature 3, a method is disclosed for synthesizing a levulinic acid ester from a cellulose-containing raw material, such as wood powder, using a catalyst quantity of organic acid with 10 or more carbon atoms in an alcohol solvent. In an example thereof, a method is disclosed in which about 20% by mole naphthalenesulfonic acid is used as a catalyst relative to cellulose in raw material wood powder and they are heated in an alcohol at 200° C. to synthesize a levulinic acid ester at a yield of 89 to 97%.

Furthermore, according to Non-Patent Literature 3, a reaction is disclosed in which methyl levulinate is synthesized from cellulose using a catalyst quantity of aluminum sulfate in methanol. In an example thereof, a method is disclosed in which about 16% by mole aluminum sulfate is used as a catalyst relative to cellulose as a raw material and they are heated in methanol at 180° C. to synthesize methyl levulinate at a yield of 44%.

According to methods described in Patent Literature 4 and an example of Non-Patent Literature 4, a reaction is disclosed in which methyl levulinate is synthesized from cellulose or a cellulose-containing raw material, such as wood powder, using a catalyst quantity of catalytic system consisting of a combination of a trifluoromethylsulfate of a Group XIII element and an organic sulfonic acid compound, at a higher yield than using each catalyst alone. For example, a method is disclosed therein in which a 0.8% by mole trifluoromethylsulfate of a Group XIII element and a 4% by mole aromatic sulfonic acid are used as catalysts relative to the raw material and they are heated in methanol at 180° C. to synthesize methyl levulinate at a yield of 65 to 75%. This method has an advantage in that the amount of acid catalyst used is further reduced, but practically has a cost problem because trifluoromethylsulfates are expensive.

CITATION LIST

Patent Literature

Patent Literature 1: Japanese Patent No. 1166813 (Claims et al.)
Patent Literature 2: U.S. Pat. No. 5,608,105 (Claims et al.)
Patent Literature 3: WO 2009/156842 A1 (Claims et al.)
Patent Literature 4: Japanese Patent No. 5366128 (Claims et al.)

Non-Patent Literature

Non-Patent Literature 1: B. F. Mckenzie, Org. Synth. 9, 50 (1929)
Non-Patent Literature 2: J. Dahlmann, Chem. Ber., 101, 4251 (1968)
Non-Patent Literature 3: L. Zhou, H. Zou, J. Nan, L. Wu, X. Yang, Y. Su, T. Lu, J. Xu, Catal. Commun., 50, 13 (2014)
Non-Patent Literature 4: K. Tominaga, A. Mori, Y. Fukushima, S. Shimada, K. Sato, Green Chem., 13, 810 (2010)

SUMMARY OF INVENTION

Technical Problem

As described above, the method for producing a levulinic acid ester by subjecting a cellulose-containing raw material or a carbohydrate-containing raw material to heat treatment in the presence of an acid in an alcohol generally requires a smaller amount of acid used than the method for producing a levulinic acid by subjecting the raw material in the presence of an acid in water and therefore have an advantage from the viewpoints of corrosion of the apparatus and disposal of post-reaction acid. However, in order to efficiently produce a levulinic acid ester with a sulfonic acid alone, a certain amount of acid is necessary. On the other hand, as for the method in which a sulfonic acid and a trifluoromethylsulfate of a Group XIII element are combined, the amount of acid used can be reduced but the high costs of trifluoromethylsulfates of Group XIII elements impede the practical use of this method. Therefore, there is strong demand for development of a catalytic system which is less expensive and requires a small amount of acid used.

The present invention has been made against a background of the above known art and provides a method for efficiently producing a levulinic acid ester from a cellulose-containing raw material or a carbohydrate-containing raw material in an alcohol solvent using an inexpensive, easily available catalytic system.

Solution to Problem

Recently, the inventors have found that if a combination of a certain kind of metal compound and an organic sulfonic acid compound is used as a catalyst, a levulinic acid ester can be produced from a cellulose-containing raw material or a carbohydrate-containing raw material, without any use of an expensive trifluoromethylsulfate, at an approximately equivalent yield to that with the use of the trifluoromethylsulfate. In this production method, the metal compound for use in reaction is inexpensive and the combination thereof with an organic sulfonic acid enables the production of a levulinic acid ester with higher efficiency than with the use of the organic sulfonic acid alone. Since an approximately equivalent yield can be achieved in a smaller amount of acid and using an inexpensive catalyst, various previous problems are overcome.

The inventors have found, as a result of intensive studies on the catalyst in the method for producing a levulinic acid ester based on the reaction having the above-described excellent features, that a levulinic acid ester can be efficiently obtained from a cellulose-containing raw material or a carbohydrate-containing raw material in an alcohol with the use of a catalytic system consisting of a combination of: at least one metal compound (exclusive of gallium acetylacetonate and indium acetylacetonate) selected from the group consisting of hydroxide salts, sulfates, nitrates, carboxylates, alkoxides, acetylacetonates, and oxides of at least one metal selected from the group consisting of metals belonging to Group XIII and Group XIV of the Periodic Table; and an organic sulfonic acid compound, and completed the present invention based on the finding.

Specifically, this application provides the following invention.

A method for producing a levulinic acid ester according to the present invention is a method for producing a levulinic acid ester by reacting at least one of a cellulose-containing raw material and a carbohydrate-containing raw material in the presence of an alcohol and a catalyst. In the method for producing a levulinic acid ester according to the present invention, use is made of, as a catalyst, a combination of: at least one metal compound (exclusive of gallium acetylacetonate and indium acetylacetonate) selected from the group consisting of hydroxide salts, sulfates, nitrates, carboxylates, alkoxides, acetylacetonates, and oxides of at least one metal selected from the group consisting of Group XIII and Group XIV of the Periodic Table; and an organic sulfonic acid.

In the method for producing a levulinic acid ester according to the present invention, the metal is preferably at least one selected from the group consisting of boron, aluminum, gallium, indium, germanium, tin, and lead.

In the method for producing a levulinic acid ester according to the present invention, the organic sulfonic acid is preferably at least one selected from the group consisting of alkyl sulfonic acids with 1 to 6 carbon atoms and aryl sulfonic acids with 6 to 24 carbon atoms.

In the method for producing a levulinic acid ester according to the present invention, the organic sulfonic acid is preferably at least one selected from the group consisting of methanesulfonic acid, ethanesulfonic acid, hexanesulfonic acid, camphorsulfonic acid, methanedisulfonic acid, ethanedisulfonic acid, propanedisulfonic acid, butanedisulfonic acid, benzenesulfonic acid, toluenesulfonic acid, naphthalenesulfonic acid, naphthalenedisulfonic acid, anthracenesulfonic acid, anthracenedisulfonic acid, pyrenesulfonic acid, and pyrenedisulfonic acid.

In the method for producing a levulinic acid ester according to the present invention, an amount of the metal compound used is preferably 0.1% to 20% by mole relative to sugar constituting part of the cellulose-containing raw material and the carbohydrate-containing raw material.

In the method for producing a levulinic acid ester according to the present invention, an amount of the organic sulfonic acid used is preferably 1% to 30% by mole relative to sugar constituting part of the cellulose-containing raw material and the carbohydrate-containing raw material.

In the method for producing a levulinic acid ester according to the present invention, an amount of the alcohol present is preferably 10 to 400 equivalents relative to sugar constituting part of the cellulose-containing raw material and the carbohydrate-containing raw material.

In the method for producing a levulinic acid ester according to the present invention, the cellulose-containing raw material or the carbohydrate-containing raw material is preferably contained in at least one raw material selected from the group consisting of wood, sawdust, wood powder, bark, paper, pulp, paper waste, bagasse, chaff, palm kernel shell, bran, rice bran, soymeal, rapeseed meal, coffee waste, tea waste, okara, corncob, corn stover, palm fiber, switchgrass, alfalfa, bamboo, grass, hay, seagrass, and seaweed.

In the method for producing a levulinic acid ester according to the present invention, a reaction temperature is preferably 160° C. to 230° C.

Advantageous Effects of Invention

According to the method of the present invention, a levulinic acid ester can be produced from a cellulose-containing raw material or a carbohydrate-containing raw material without any use of an expensive compound as a catalyst. The cost problem in the known art that has impeded its practical use can be solved.

Furthermore, according to the method of the present invention, a levulinic acid ester can be produced from a cellulose-containing raw material or a carbohydrate-containing raw material in a smaller amount of acid and with higher efficiency than before. The produced levulinic acid ester can be separated and recovered by a distillation process. Since the amount of acid used is small and the product is an ester compound, the apparatus cost for production and environmental burden can be significantly reduced.

DESCRIPTION OF EMBODIMENTS

There is no particular limitation as to the kind of the cellulose-containing raw material or the carbohydrate-containing raw material for use as a raw material and it includes every cellulose-containing raw material or carbohydrate-containing raw material which has heretofore been used as a raw material for this kind of levulinic acid or levulinic acid ester. Examples of such cellulose-containing raw materials and carbohydrate-containing raw materials include celluloses or mixtures thereof and materials containing various kinds of biomass-derived carbohydrates.

Among carbohydrates, examples that can be cited as monosaccharides include glucose, fructose, galactose, and mannose and examples that can be cited as polysaccharides include starch and cellulose. Examples of the cellulose-containing raw materials include various kinds of wood, such as cedar, Oregon pine, and *eucalyptus*, sawdust, wood powder, bark, paper, pulp, paper waste, bagasse, chaff, palm kernel shell, bran, rice bran, soymeal, rapeseed meal, coffee waste, tea waste, okara, corncob, corn stover, palm fiber, switchgrass, alfalfa, bamboo, grass, hay, seagrass, and seaweed.

These cellulose-containing raw materials or carbohydrate-containing raw materials may be used alone or, if the raw material itself is a mixture of them, it may be used in the form of a mixture without isolation. Furthermore, the raw material may be supplied in a moisture state or may be supplied after undergoing a drying process.

In the present invention, not only a catalyst but also an alcohol are present during the reaction for producing a levulinic acid ester from at least one of the cellulose-containing raw material and the carbohydrate-containing raw material. The amount of alcohol present is, but not particularly limited to, preferably 10 to 1000 equivalents (401 g/L to 4 g/L with the use of methanol as the alcohol) and more preferably 20 to 100 equivalents (200 g/L to 40 g/L with the use of methanol as the alcohol) relative to sugar constituting part of the cellulose-containing raw material or the carbohydrate-containing raw material.

If the amount of alcohol present is less than 10 equivalents relative to sugar constituting part of the cellulose-containing raw material and the carbohydrate-containing raw material, the selectivity and yield of the levulinic acid ester may decrease. Also, if the amount of alcohol present is more than 400 equivalents relative to sugar constituting part of the cellulose-containing raw material and the carbohydrate-containing raw material, the selectivity and yield of the levulinic acid ester may decrease.

Examples of the alcohol present that can be used include, but not necessarily limited to, methanol, ethanol, propanol, butanol, pentanol, hexanol, heptanol, octanol, nonanol, and decyl alcohol. Examples of the alcohol are more preferably primary alcohols of them and still more preferably methanol, ethanol, 1-propanol, and 1-butanol. These alcohols may be used alone or any of them may be mixed, but, if they are mixed, levulinic acid esters having a plurality of alkyl groups may be concurrently generated.

As a metal contained in the metal compound used as a catalyst and containing a metal belonging to Group XIII or Group XIV of the Periodic Table, a compound of any metal selected from the group consisting of boron, aluminum, gallium, indium, germanium, tin, and lead can be selected. Among them, Group XIII metals are preferably used and, particularly, aluminum is more preferably used. The form (type) of the compound can be selected from hydroxide salt, sulfate, nitrate, carboxylate, alkoxide, acetylacetonate, oxide, and so on. The form of the compound is more preferably hydroxide salt, sulfate or alkoxide. These compounds may be used in the form of a salt soluble in a solvent or may be used in the form of a salt insoluble in a solvent.

The amount of metal compound used is preferably 0.1% to 20% by mole and more preferably 0.5% to 5% by mole relative to sugar constituting part of the cellulose-containing raw material or the carbohydrate-containing raw material.

In the present invention, the reaction is performed in the co-presence of not only the above metal compound but also an organic sulfonic acid. The kind of organic sulfonic acid that is preferably used can be selected from the group consisting of alkyl sulfonic acids with 1 to 6 carbon atoms and aryl sulfonic acids with 6 to 24 carbon atoms. The organic sulfonic acid is preferably methanesulfonic acid, ethanesulfonic acid, hexanesulfonic acid, camphorsulfonic acid, methanedisulfonic acid, ethanedisulfonic acid, propanedisulfonic acid, butanedisulfonic acid, benzenesulfonic acid, toluenesulfonic acid, naphthalenesulfonic acid, naphthalenedisulfonic acid, anthracenesulfonic acid, anthracenedisulfonic acid, pyrenesulfonic acid or pyrenedisulfonic acid and more preferably benzenesulfonic acid, toluenesulfonic acid or naphthalenesulfonic acid.

The amount of organic sulfonic acid used is preferably 1% to 30% by mole and more preferably 5% to 20% by mole relative to sugar constituting part of the cellulose-containing raw material and the carbohydrate-containing raw material.

The reaction method in the present invention is preferably, but not particularly limited to, the method of adding a cellulose-containing raw material or a carbohydrate-containing raw material into an alcohol containing a catalyst quantity of metal compound and organic sulfonic acid and reacting them by the application of heat. Alternatively, a catalyst quantity of metal compound and organic sulfonic acid may be previously sufficiently reacted in an alcohol, as necessary, with the application of heat, a cellulose-containing raw material or a carbohydrate-containing raw material may be then added to them, and the mixture may be reacted by the application of heat.

The reaction temperature is preferably in a range of 160° C. to 230° C. and particularly preferably in a range of 180° C. to 200° C. If the reaction temperature is lower than the above, the reaction rate may be reduced. On the other hand, if the reaction temperature is higher than the above, the production of an ether compound due to intermolecular dehydration reaction of the alcohol may become significant and the yield of the desired levulinic acid ester may be reduced.

Furthermore, the pressure and atmosphere during the reaction need not be limited, but, generally, a pressure-tight reaction container, such as an autoclave, is preferably used and the reaction is preferably performed in a nitrogen atmosphere under a pressure of about five or more atmospheres (preferably 10 to 50 atmospheres, more preferably 20 to 40 atmospheres, and still more preferably 28 to 32 atmospheres). If the atmospheric pressure is less than five atmospheres, the reaction temperature may not sufficiently reach a desired temperature, thus reducing the reaction rate. On the other hand, if nitrogen gas of over 50 atmospheres is encapsulated, breakage, failure and so on due to explosion or the like of the apparatus may occur and, therefore, an apparatus cost for preventing such breakage and failure increases.

EXAMPLES

Next, the present invention will be described in more detail with reference to examples but is not at all limited to these examples.

Example 1<Combined Test of Various Group XIII Metal Compounds and Organic Sulfonic Acid)

Example 1-1

An amount of 405 mg (2.5 mmol in glucose equivalent) of cellulose, 0.02 mmol of Al(OH)$_3$, and 0.2 mmol of p-toluenesulfonic acid (PTSA) were added into a stainless-steel autoclave having a volume of 50 ml and the mixture was reacted using 20 ml of methanol as a solvent by heating them at 180° for five hours in a nitrogen atmosphere under a pressure of 0.5 atmospheres. After the reaction, the reaction solution was cooled to room temperature and analyzed by liquid chromatography. As a result, it was confirmed that methyl levulinate was obtained at a yield of 64%.

Example 1-2

Reaction was performed in the same manner as in Example 1-1 except that 0.01 mmol of Al$_2$(SO$_4$)$_3$ was used in place of Al(OH)$_3$ in Example 1-1, so that it was confirmed that a methyl levulinate was obtained at a yield of 63%.

Example 1-3

Reaction was performed in the same manner as in Example 1-1 except that Al(OEt)$_3$ was used in place of Al(OH)$_3$ in Example 1-1, so that it was confirmed that a methyl levulinate was obtained at a yield of 68%.

Example 1-4

Reaction was performed in the same manner as in Example 1-1 except that Al(OAc)$_3$ was used in place of Al(OH)$_3$ in Example 1-1, so that it was confirmed that a methyl levulinate was obtained at a yield of 65%.

Example 1-5

Reaction was performed in the same manner as in Example 1-1 except that Al(acac)$_3$ was used in place of Al(OH)$_3$ in Example 1-1, so that it was confirmed that a methyl levulinate was obtained at a yield of 71%.

Example 1-6

Reaction was performed in the same manner as in Example 1-1 except that 0.01 mmol of Al$_2$O$_3$ was used in place of Al(OH)$_3$ in Example 1-1, so that it was confirmed that a methyl levulinate was obtained at a yield of 50%.

Example 1-7

Reaction was performed in the same manner as in Example 1-1 except that In(OH)$_3$ was used in place of Al(OH)$_3$ in Example 1-1, so that a methyl levulinate was obtained at a yield of 61%.

Example 1-8

Reaction was performed in the same manner as in Example 1-1 except that B(OEt)$_3$ was used in place of Al(OH)$_3$ in Example 1-1, so that it was confirmed that a methyl levulinate was obtained at a yield of 54%.

The above results are shown in Table 1.

TABLE 1

Combined Test of Various Group XIII Metal Compounds and Organic Sulfonic Acid

| Example | Metal Compound/ mol % | Organic Sulfonic Acid/ mol % | Temperature/ ° C. | Hours/h | Yield/% |
| --- | --- | --- | --- | --- | --- |
| 1-1 | Al(OH)$_3$/ 0.8 | PTSA/ 8.0 | 180 | 5 | 64 |
| 1-2 | Al$_2$(SO$_4$)$_3$/ 0.4 | PTSA/ 8.0 | 180 | 5 | 63 |
| 1-3 | Al(OEt)$_3$/ 0.8 | PTSA/ 8.0 | 180 | 5 | 68 |
| 1-4 | Al(OAc)$_3$/ 0.8 | PTSA/ 8.0 | 180 | 5 | 65 |
| 1-5 | Al(acac)$_3$/ 0.8 | PTSA/ 8.0 | 180 | 5 | 71 |
| 1-6 | Al$_2$O$_3$/ 0.4 | PTSA/ 8.0 | 180 | 5 | 50 |
| 1-7 | In(OH)$_3$/ 0.8 | PTSA/ 8.0 | 180 | 5 | 61 |
| 1-8 | B(OEt)$_3$/ 0.8 | PTSA/ 8.0 | 180 | 5 | 54 |

Example 2<Combined Test of Various Group XIV Metal Compounds and Organic Sulfonic Acid)

Example 2-1

An amount of 405 mg (2.5 mmol in glucose equivalent) of cellulose, 0.02 mmol of GeO$_2$, and 0.2 mmol of p-toluenesulfonic acid (PTSA) were added into a stainless-steel autoclave having a volume of 50 ml and the mixture was reacted using 20 ml of methanol as a solvent by heating them at 180° for five hours in a nitrogen atmosphere under a pressure of 0.5 atmospheres. After the reaction, the reaction solution was cooled to room temperature and analyzed by liquid chromatography. As a result, it was confirmed that methyl levulinate was obtained at a yield of 60%.

Example 2-2

Reaction was performed in the same manner as in Example 2-1 except that Sn(acac)$_3$ was used in place of GeO$_2$ in Example 2-1, so that it was confirmed that a methyl levulinate was obtained at a yield of 56%.

Example 2-3

Reaction was performed in the same manner as in Example 2-1 except that Sn(OMe)$_2$ was used in place of GeO$_2$ in Example 2-1, so that it was confirmed that a methyl levulinate was obtained at a yield of 52%.

The above results are shown in Table 2.

TABLE 2

Combined Test of Various Group XIV Metal Compounds and Organic Sulfonic Acid

| Example | Metal Compound/ mol % | Organic Sulfonic Acid/ mol % | Temperature/ ° C. | Hours/h | Yield/% |
| --- | --- | --- | --- | --- | --- |
| 2-1 | GeO$_2$/ 0.8 | PTSA/ 8.0 | 180 | 5 | 60 |
| 2-2 | Sn(acac)$_3$/ 0.8 | PTSA/ 8.0 | 180 | 5 | 56 |
| 2-3 | Sn(OMe)$_2$/ 0.8 | PTSA/ 8.0 | 180 | 5 | 52 |

Example 3<Test Using Various Organic Sulfonic Acids>

Example 3-1

An amount of 405 mg (2.5 mmol in glucose equivalent) of cellulose, 0.02 mmol of Al (acac)$_3$, and 0.2 mmol of benzenesulfonic acid (BSA) were added into a stainless-steel autoclave having a volume of 50 ml and the mixture was reacted using 20 ml of methanol as a solvent by heating them at 180° for five hours in a nitrogen atmosphere under a pressure of 0.5 atmospheres. After the reaction, the reaction solution was cooled to room temperature and analyzed by liquid chromatography. As a result, it was confirmed that methyl levulinate was obtained at a yield of 61%.

Example 3-2

Reaction was performed in the same manner as in Example 3-1 except that 2-naphthalenesulfonic acid (NSA) was used in place of benzenesulfonic acid in Example 3-1, so that it was confirmed that a methyl levulinate was obtained at a yield of 74%.

Example 3-3

Reaction was performed in the same manner as in Example 3-1 except that methanedisulfonic acid (MDSA) was used in place of benzenesulfonic acid in Example 3-1, so that it was confirmed that a methyl levulinate was obtained at a yield of 63%.

Example 3-4

Reaction was performed in the same manner as in Example 3-1 except that ethanedisulfonic acid (EDSA) was used in place of benzenesulfonic acid in Example 3-1, so that it was confirmed that a methyl levulinate was obtained at a yield of 70%.

Example 3-5

Reaction was performed in the same manner as in Example 3-1 except that propanedisulfonic acid (PDSA) was used in place of benzenesulfonic acid in Example 3-1, so that it was confirmed that a methyl levulinate was obtained at a yield of 66%.

The above results are shown in Table 3.

TABLE 3

| | Test Using Various Organic Sulfonic Acids | | | | |
|---|---|---|---|---|---|
| Example | Metal Compound/ mol % | Organic Sulfonic Acid/ mol % | Temperature/ °C. | Hours/h | Yield/% |
| 3-1 | Al(acac)$_3$/ 0.8 | BSA/ 8.0 | 180 | 5 | 61 |
| 3-2 | Al(acac)$_3$/ 0.8 | NSA/ 8.0 | 180 | 5 | 74 |
| 3-3 | Al(acac)$_3$/ 0.8 | MDSA/ 8.0 | 180 | 5 | 63 |
| 3-4 | Al(acac)$_3$/ 0.8 | EDSA/ 8.0 | 180 | 5 | 70 |
| 3-5 | Al(acac)$_3$/ 0.8 | PDSA/ 8.0 | 180 | 5 | 66 |

Example 4<Test Using Various Biomass Raw Materials>

Example 4-1

An amount of 500 mg of cedar powder (having a cellulose content of 43.6%), 0.02 mmol of Al(acac)$_3$, and 0.2 mmol of p-toluenesulfonic acid were added into a stainless-steel autoclave having a volume of 50 ml and the mixture was reacted using 20 ml of methanol as a solvent by heating them at 180° for five hours in a nitrogen atmosphere under a pressure of 0.5 atmospheres. After the reaction, the reaction solution was cooled to room temperature and analyzed by liquid chromatography. As a result, it was confirmed that methyl levulinate was obtained at a yield of 80%.

Example 4-2

Reaction was performed in the same manner as in Example 3-1 except that *eucalyptus* powder (having a cellulose content of 44.7%) was used in place of cedar powder in Example 3-1, so that it was confirmed that a methyl levulinate was obtained at a yield of 84%.

The above results are shown in Table 4.

TABLE 4

| | Test Using Various Biomass Raw Materials | | | | | |
|---|---|---|---|---|---|---|
| Example | Wood Species/ wt % | Metal Compound/ mmol | Organic Sulfonic Acid/ mmol | Temperature/ °C. | Hours/ h | Yield/ % |
| 4-1 | Cedar/ 2.5 | Al(acac)$_3$/ 0.02 | PTSA/ 0.2 | 180 | 5 | 80 |
| 4-2 | Eucalyptus/ 2.5 | Al(acac)$_3$/ 0.02 | PTSA/ 0.2 | 180 | 5 | 84 |

Example 5<Test Using Pulp Raw Materials>

Example 5-1

An amount of 500 mg of alkali-cooked pulp (having a glucose content of 75.2%) rinsed in water, 0.02 mmol of Al(acac)$_3$, and 0.2 mmol of p-toluenesulfonic acid were added into a stainless-steel autoclave having a volume of 50 ml and the mixture was heated, using 20 ml of methanol as a solvent, at 180° for five hours in a nitrogen atmosphere under a pressure of 0.5 atmospheres. Thereafter, the reaction solution was cooled to room temperature and analyzed by liquid chromatography. As a result, it was confirmed that methyl levulinate was obtained at a yield of 85%.

Example 5-2

Reaction and analysis were conducted in the same manner as in Example 5-1 except that alkali-oxygen-cooked cedar pulp (having a glucose content of 71.9%) was used in place of alkali-cooked pulp rinsed in water in Example 5-1, so that it was confirmed that a methyl levulinate was obtained at a yield of 83%.

Example 5-3

Reaction and analysis were conducted in the same manner as in Example 5-1 except that alkali-oxygen-cooked *eucalyptus* pulp (having a glucose content of 78.5%) was used in place of alkali-cooked pulp rinsed in water in Example 5-1, so that it was confirmed that a methyl levulinate was obtained at a yield of 86%.

Example 5-4

Reaction and analysis were conducted in the same manner as in Example 5-1 except that soda-AQ cedar pulp (having a glucose content of 71.1%) was used in place of alkali-cooked pulp rinsed in water in Example 5-1, so that it was confirmed that a methyl levulinate was obtained at a yield of 90%.

Example 5-5

Reaction and analysis were conducted in the same manner as in Example 5-1 except that soda-AQ *eucalyptus* pulp (having a glucose content of 70.6%) was used in place of alkali-cooked pulp rinsed in water in Example 5-1, so that it was confirmed that a methyl levulinate was obtained at a yield of 89%.

The results of Examples 5-1 to 5-4 are shown in Table 5.

TABLE 5

Test Using Various Biomass Raw Materials

| Example | Raw Material/ wt % | Metal Compound/ mmol | Organic Sulfonic Acid/ mmol | Temperature/ °C. | Hours/ h | Yield/ % |
|---|---|---|---|---|---|---|
| 5-1 | Alkali-cooked cedar pulp/ 2.5 | $Al(acac)_3$/ 0.02 | PTSA/ 0.2 | 180 | 5 | 85 |
| 5-2 | Alkali-oxygen-cooked cedar pulp/ 2.5 | $Al(acac)_3$/ 0.02 | PTSA/ 0.2 | 180 | 5 | 83 |
| 5-3 | Alkali-oxygen-cooked eucalyptus pulp/ 2.5 | $Al(acac)_3$/ 0.02 | PTSA/ 0.2 | 180 | 5 | 86 |
| 5-4 | Soda-AQ cedar pulp/ 2.5 | $Al(acac)_3$/ 0.02 | PTSA/ 0.2 | 180 | 5 | 90 |
| 5-5 | Soda-AQ eucalyptus pulp/ 2.5 | $Al(acac)_3$/ 0.02 | PTSA/ 0.2 | 180 | 5 | 89 |

Comparative Examples<Comparison with Known Production Methods>

Comparative Example 1

An amount of 405 mg (2.5 mmol in glucose equivalent) of cellulose and 0.2 mmol of p-toluenesulfonic acid (PISA) were added into a stainless-steel autoclave having a volume of 50 ml and the mixture was reacted using 20 ml of methanol as a solvent by heating them at 180° for five hours in a nitrogen atmosphere under a pressure of 0.5 atmospheres. After the reaction, the reaction solution was cooled to room temperature and analyzed by liquid chromatography. As a result, it was confirmed that methyl levulinate was obtained at a yield of 48%.

Comparative Example 2

Reaction was performed in the same manner as in Comparative Example 1 except that 0.02 mmol of $In(OTf)_3$ and 0.2 mmol of p-toluenesulfonic acid were used as catalysts, so that it was confirmed that a methyl levulinate was obtained at a yield of 73%.

The above results are shown in Table 6.

TABLE 6

Comparison with Known Production Methods

| Comparative Example | Metal Compound/ mol % | Organic Sulfonic Acid/ mol % | Temperature/ °C. | Hours/h | Yield/% |
|---|---|---|---|---|---|
| 1 | — | PTSA/ 8.0 | 180 | 5 | 48 |
| 2 | $In(OTf)_3$/ 0.8 | PTSA/ 8.0 | 180 | 5 | 73 |

It can be seen from Comparative Example 1 that, as performed in the present production method, with the use of, as a catalyst, a combination of: at least one compound selected from the group consisting of hydroxide salts, sulfates, nitrates, carboxylates, alkoxides, acetylacetonates, and oxides of at least one metal selected from the group consisting of metals belonging to Group XIII and Group XIV of the Periodic Table; and an organic sulfonic acid, methyl levulinate can be obtained at a higher yield than when produced with an organic sulfonic acid alone as a catalyst.

It can be seen from Comparative Example 2 that, as performed in the present production method, with the use of, as a catalyst, a combination of: at least one metal compound selected from the group consisting of hydroxide salts, sulfates, nitrates, carboxylates, alkoxides, acetylacetonates, and oxides of at least one metal selected from the group consisting of metals belonging to Group XIII and Group XIV of the Periodic Table; and an organic sulfonic acid, methyl levulinate can be obtained, in spite of using the catalytic system less expensive than in the methods disclosed in Patent Literature 4 and Non-Patent Literature 4, at an approximately equivalent yield to that in these methods.

INDUSTRIAL APPLICABILITY

The present invention is useful for producing a levulinic acid ester more inexpensively and efficiently than in known production methods by using sugars, various carbohydrates, such as cellulose, or various carbohydrate-containing materials as raw materials. Not only plants themselves, including wood, can be directly used as carbohydrates which are possible raw materials, but also carbohydrate-containing wastes, such as waste paper, and sugar or starch derived from the wastes can be used. In addition, the resultant levulinic acid ester can be used as a fuel additive, a polymer source material, a medicine or agrochemical intermediate or so on, which contributes to reduction in dependence of the chemical industry on fossil sources.

The invention claimed is:

1. A method for producing a levulinic acid ester by reacting a carbohydrate-containing raw material in the presence of an alcohol and a catalyst, the method using, as a catalyst, a combination of: at least one metal compound (exclusive of gallium acetylacetonate and indium acetylacetonate) selected from the group consisting of hydroxide salts, sulfates, nitrates, carboxylates, alkoxides, acetylacetonates, and oxides of at least one metal selected from the group consisting of metals belonging to Group XIII and Group XIV of the Periodic Table; and an organic sulfonic acid; wherein
   the carbohydrate-containing raw material is contained in at least one raw material selected from the group consisting of cedar powder, *eucalyptus* powder, alkali-cooked cedar pulp, alkali-oxygen-cooked cedar pulp, alkali-oxygen-cooked *eucalyptus* pulp, soda-AQ cedar pulp, and soda-AQ *eucalyptus* pulp.

2. The method for producing a levulinic acid ester according to claim 1, wherein the metal is at least one selected from the group consisting of boron, aluminum, gallium, indium, germanium, tin, and lead.

3. The method for producing a levulinic acid ester according to claim 1, wherein the organic sulfonic acid is at least one selected from the group consisting of alkyl sulfonic acids with 1 to 6 carbon atoms and aryl sulfonic acids with 6 to 24 carbon atoms.

4. The method for producing a levulinic acid ester according to claim 1, wherein the organic sulfonic acid is at least one selected from the group consisting of methanesulfonic acid, ethanesulfonic acid, hexanesulfonic acid, camphorsulfonic acid, methanedisulfonic acid, ethanedisulfonic acid, propanedisulfonic acid, butanedisulfonic acid, benzenesulfonic acid, toluenesulfonic acid, naphthalenesulfonic acid, naphthalenedisulfonic acid, anthracenesulfonic acid, anthracenedisulfonic acid, pyrenesulfonic acid, and pyrenedisulfonic acid.

5. The method for producing a levulinic acid ester according to claim 1, wherein an amount of the metal compound used is 0.1% to 20% by mole relative to sugar constituting part of the carbohydrate-containing raw material.

6. The method for producing a levulinic acid ester according to claim 1, wherein an amount of the organic sulfonic acid used is 1% to 30% by mole relative to sugar constituting part of the carbohydrate-containing raw material.

7. The method for producing a levulinic acid ester according to claim 1, wherein an amount of the alcohol present is 10 to 400 equivalents relative to sugar constituting part of carbohydrate-containing raw material.

8. The method for producing a levulinic acid according to claim 1, wherein a reaction temperature is 160° C. to 230° C.

9. The method for producing a levulinic acid ester according to claim 1, wherein the catalyst is Al(acac)$_3$ and the organic sulfonic acid is p-toluenesulfonic acid.

* * * * *